United States Patent [19]

Shine

[11] 4,278,936
[45] Jul. 14, 1981

[54] BIOLOGICAL CELL PARAMETER CHANGE TEST METHOD AND APPARATUS

[75] Inventor: Ian B. Shine, Lexington, Ky.

[73] Assignee: Coulter Electronics, Inc., Hialeah, Fla.

[21] Appl. No.: 118,727

[22] Filed: Feb. 5, 1980

[51] Int. Cl.³ .............................................. G01N 27/00
[52] U.S. Cl. .............................. 324/71 CP; 235/92 PC
[58] Field of Search ................. 307/246; 235/92 PC; 324/71 CP

[56] References Cited

U.S. PATENT DOCUMENTS

| | | | |
|---|---|---|---|
| 2,656,508 | 10/1953 | Coulter | 324/71 CP |
| 3,259,842 | 7/1968 | Coulter et al. | 324/71 CP |
| 3,982,183 | 9/1976 | Collineau et al. | 324/71 CP |
| 4,041,385 | 8/1977 | Gulliford et al. | 324/71 CP |

*Primary Examiner*—Michael J. Tokar
*Attorney, Agent, or Firm*—Gerald R. Hibnick

[57] ABSTRACT

By subjecting cells, such as blood cells, tissue cells, and bone marrow cells, to hypotonic solutions having different osmolalities, the cells will rapidly attain a change in volume and electrical resistance parameters, which change is measurable, for example, by a Coulter Counter® particle measuring instrument. The relationship between change in cell resistance or cell volume and osmolality provides a discriminator between normality, different diseases, and certain inherited differences.

24 Claims, 3 Drawing Figures

BIOLOGICAL CELL PARAMETER CHANGE TEST METHOD AND APPARATUS

FIELD OF THE INVENTION

The invention concerns a new discriminator employable in medical screening and testing. More specifically, the invention pertains to method and apparatus which, in a preferred embodiment, the electrical resistance of cells, such as red blood cells, is changed by osmosis. Such cell parameter change generates a set of related data, which defines a pattern which is a characteristic of the health or physiological condition of the human or animal source of the cell sample.

BACKGROUND OF THE INVENTION

The study of human cells for medical screening, diagnostic and other medical purposes is well known. For example, red blood cell count, mean cell volume (MCV), hemoglobin content and hematocrit are well known and commonly employed red blood cell parameters used in medical study and patient care. It is typical to free the hemoglobin from the red cells by lysis, i.e., destruction of the cells. Such cell destruction is accomplished by dissolving or rupturing the stroma of the cell and also is termed hemolysis.

It is well known that the osmotic pressure of solutions, i.e., their osmolality, such as saline solutions, varies with their concentration and type of solutes, and that the difference between the osmotic pressure within a cell and that of its surrounding environment causes the cell to change in volume and electrical resistance.

The so-called physiological saline solution is isotonic and cells suspended in such a solution will neither swell nor shrink in size or volume, nor will their electrical resistance change. Distilled water is hypotonic with respect to the isotonic solution in which blood cells reside within the human body. Saline solutions can be isotonic, hypotonic or hypertonic, depending upon their concentration.

A relatively well known, but less often employed, red cell test is osmotic fragility, which is a measurement of rate of the hemolysis of the cell under controlled changes of osmotic pressure. The Fragiligraph is an instrument which measures osmotic fragility and, over a period of approximately five minutes, hemolizes an increasing number of red cells in a sample, optically measures the amount of released hemoglobin, and plots a characteristic ogee (S shaped) curve or its derivative. The abscissa of the curve is time and the ordinate is the amount of hemolysis. A few variations in curve shape have been recognized and related to different health conditions.

It is necessary to understand the relationship between osmotic pressure and hemolysis to be able to appreciate that the present invention is based upon a treatment and measurement of the cells which does not destroy the cell stroma and thus differs from hemolysis.

Cell and particle counting and measuring instruments, examples being those sold under the trademark Coulter Counter ® by Coulter Electronics, Inc., Hialeah, Fla., employ electronic sensing means which directly respond to the electrical resistance of each cell to count and measure each cell and progressively record cell parameters of a sample of cells in an isotonic solution. The Coulter Counter ® particle measuring instruments operate upon the well known and well documented principle of particle and cell measurement employing a sensing aperture path, which also is disclosed in Coulter U.S. Pat. No. 2,656,508 and improvement U.S. Pat. No. 3,259,842. A form of MCV measuring apparatus especially useful with a Coulter Counter ® instrument is taught in U.S. Pat. No. 3,473,010. The response of a Coulter Counter ® electric sensor is influenced at least by the shape, deformability and flow rate of the microscopic item being measured as it flows through the sensing aperture path. Since most cells are subject to some deformation as they pass through the sensing aperture path, their electrical resistance measurement and the recorded measured volume may differ from their true volume. To distinguish between true volume and measured volume, the term "apparent volume" will be employed herein to refer to measured volume.

SUMMARY OF THE INVENTION

By subjecting cells to solutions having several different hypotonic concentrations, the electrical resistance parameter of the cells changes, the resistance increasing to a peak and then falling as osmolality decreases. If the resistance measurement is used to define apparent volume and then record MCV, these three parameters will provide correlatable data. Since the several hypotonic solutions will cause cell volume changes, there also will result some true volume data. A plotting or charting of the induced cell parameter changes, relative to the hypotonic concentration, provides data and a pattern or curve characteristic of the nature of the cell, from which some inferences can be made about the health or physiological condition of the cell donor. The data maxima and the distribution therearound, and likewise the amplitude, location and shape of the peak of the curve, and the skew and slope of the curve portions form a discriminator by which medical diagnosis can be made.

Apparatus, which provides the sequence of hypotonic concentrations and measures as well as correlates the cell parameter changes with the hypotonic concentrations, automates my cell test methodology and forms a portion of the invention. A preferred embodiment of such apparatus includes a Coulter Counter ® type of cell measuring instrument, which responds to the electrical resistance of each cell.

Although my invention employs at least one hypotonic solution to change the cell parameter measured value, it does not measure hemolysis, nor are osmotic fragility curves generated. My invention provides a new discriminator not to be confused with the osmotic fragility curve, nor with the typical measurement of MCV, which usually is obtained in an isotonic environment.

DETAILED DESCRIPTION OF THE PREFERRED EMBODIMENTS

My cell parameter change test method can be carried out manually as well as semiautomatically and automatically. The test recognizes and employs the fact that cells, for example red blood cells, function as osmometers and rapidly will change their volume and electrical resistance in a hypotonic solution and attain a new cell volume and resistance which is stable for a duration sufficient for cell parameter change measurement to be obtained. The amount of cell change depends primarily upon the osmolality of the hypotonic solution, the properties of the cell membrane and the genotype of the cell contents. Extensive experimentation with my invention has verified that blood samples from normal individuals and diseased patients provide reproducible data, from which tables and curves can be obtained, an example of which is shown in FIG. 1.

A cell, such as red, white or platelet, immersed in a hypotonic electrolyte, increases in its measured resistance, reaches a peak resistance measurement, and rapidly returns towards its original resistance. Concomitantly, the cell undergoes correlated, though not identical, changes in cell volume, at least in solutions between 350 and 140 mOsm/kg. After reaching the peak volume, a cell reduces volume more rapidly than it reduces resistance; hence, at least one reason for the difference between true volume and "apparent volume," which is discussed hereinabove. These osmotically induced dynamic changes in the parameters of cells can be reproduced by measuring the change induced at a series of particular osmolalities and fitting them together in a graph. The graph represents the dynamic changes in the same way as a movie simulates movement. The pattern of dynamic change has a characteristic size, shape and position in a normal healthy individual and characteristic differences or abnormalities in several disease states, two examples of which are set forth in FIG. 1.

Figure 1:
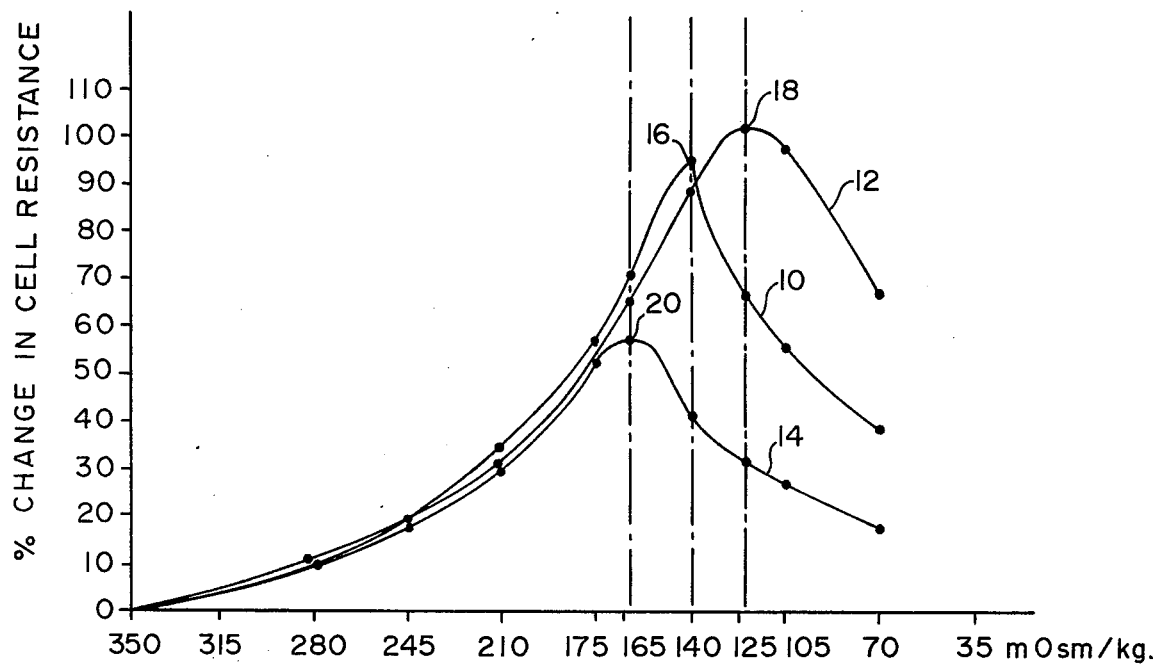
FIG. 1 is a graph of a set of curves of red blood cell relative electrical resistance versus osmolality, for three different physiological conditions.

FIG. 1 shows the curves 10, 12 and 14, respectively representative of three groups of individuals having normal blood, those with beta thalassaemia minor, and individuals having hereditary spherocytosis. The manner of collecting and treating the blood samples to attain these curves will be detailed below. However, it first is important to appreciate that these curves and the ordinate and abscissa data, which can be charted, define a new and unambiguous discriminator for various health conditions. As shown in FIG. 1, its abscissa scale is in milliosmoles per kilogram (mOsm/kg), representing the osmotic strength of the saline solution or diluent in which the cells are immersed. One such diluent is Isoton ® II, which is the "isotonic" diluent typically used by the Coulter Counter ® electronic particle counting and sizing apparatus which was employed in the development of my test method, and can be the meter shown in FIGS. 2 and 3. Other solutions capable of varying osmolality can be employed to suit the apparatus or manual utilization of my test method. Physiological saline has an osmolality of approximately 285 mOsm/kg and is isotonic. The ordinate of FIG. 1 represents the percent change of red blood cell electrical resistance, with zero percent of increase being at the origin. Since the MCV readout by a Coulter Counter ® is based upon the resistance of the cell sample, the ordinate scale could be in percent of change of MCV.

A quick inspection of FIG. 1 easily reveals that the three curves 10, 12 and 14 are different from each other in several significant ways. The curve 10, which is typical of a normal person, has a peak 16 which is pointed sharply at approximately 95% increase on the ordinate, is positioned close to 140 mOsm and is relatively symmetrical with respect to its leading and trailing sides and thus is not skewed. The curve 12, representing beta thalassaemia minor, exhibits a rounded peak 18 of 103% increase on the ordinate near 125 mOsm, with some rightward skewing. The hereditary spherocytosis representative curve 14 has a much lower peak 20 of approximately 58% on the ordinate near 165 mOsm. The sides of the curve 14 are much more divergent than those of the curves 10 and 12. Although a complete set of data points for either a plotting of these curves or a numeric charting will be more informative, a few data points can be sufficiently informative for some medical screening and some diagnostic purposes. For example, since the normal curve is sharply peaked at 140 mOsm/kg, a simple screening tool would require very few measurements near the peak osmolality. Even a correlation of ordinate and abscissa for a single point could be useful for screening. The development of cell parameter change related curves by my methodology for other health conditions reveals significant, narrow measuring ranges useful for screening purposes.

It is to be appreciated that different measuring instruments, techniques, diluents, etc., could generate some shifts from the curves and data typified in FIG. 1. Such shifts would be somewhat generally uniform for all data and curves developed by the specific testing means and thus comparative data and curves would remain distinctive from one another. For example, an optical instrument for measuring MCV might "see" the volume change of the cells differently than the "apparent volume," cell resistance measuring electronic sensor of a Coulter Counter ®. Hence, the amplitude data for the curves obtained by optical means might be attenuated as compared to that obtained by a Coulter Counter ® instrument. Also, experimentation has indicated that, in different health conditions, cells exhibit different tendencies and capabilities to be deformed, such as when passing through the sensor of a Coulter Counter ® cell analyzer. Such deformability or turgidity characteristic of cells is believed to be one discrimination parameter which is enhanced by employing a Coulter Counter ® type of instrument for my cell parameter change test method.

Another testing variable is pH. It has been found that optimal pH, when using a Coulter Counter ® particle analyzer, is 7.4 pH. A change in pH from optimum causes changes in peak amplitudes and shifts of the peak locations relative to osmolality. If the diluent is saline or other material and is buffered adequately, as is known in the art, then even at a dilution of 35 mOsm/kg, the pH does not change appreciably. Isoton ® II is adequately buffered.

I have noted that there are some conditions, variant hemoglobins for example, which are more capable of identification at pH's other than 7.4; hence, pH control also is a parameter which enhances my test methodology.

Temperature and freshness of the sample, such as a blood sample, can cause some differences in the data obtained. For blood, normal laboratory temperature in the vicinity of 22° C. is adequate. Both blood tested on the same day of collection, and also blood stored at 4° C. until being prepared for testing, proved suitable. However, older blood samples also have yielded acceptable test data. Both venous and capillary blood, with or without anticoagulant, for example with disodium or tripotassium EDTA or sodium heparin, can be employed in my test methodology. Also acceptable without need for anticoagulation is umbilical cord blood, which might be used for prenatal diagnosis.

The manual preparation of the samples for use in my test can be accomplished by diluting the collected sample with several different concentrations of a diluent, such as buffered isotonic saline, Isoton ® II, or the like. The concentration ratios or their equivalent osmolality form the abscissa, as shown in FIG. 1. The cells undergo parameter change almost immediately and then are ready for measurement. Several cell sample "batches," each in a diluent of different osmolality and thereby with a different electrical resistance depending upon the cell characteristics, can be introduced manually into and processed separately and sequentially by the cell measuring apparatus. The set of data thus can be obtained and charted and the plot of electrical resistance versus osmolality or diluent concentration developed, as shown in FIG. 1. Thereupon, the obtained data and/or curve can be compared to a pre-established family of curves and/or data, each representing a different health or physiological condition. Such comparison can be used in screening and diagnostic determinations.

Figure 2:
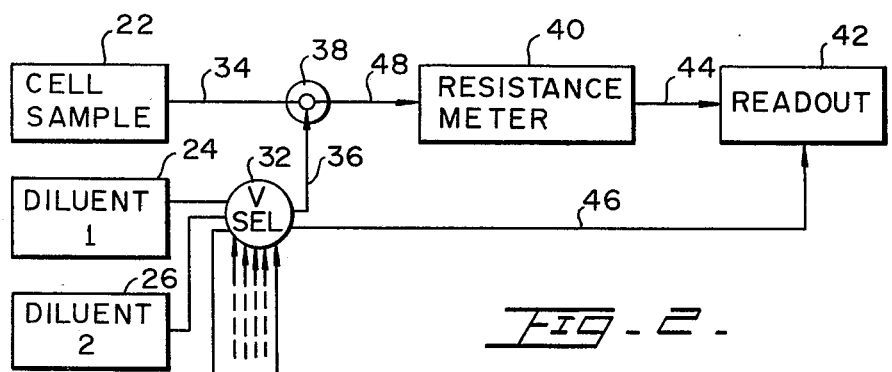
FIG. 2 is one embodiment of apparatus for generating the curves of FIG. 1.
Figure 3:
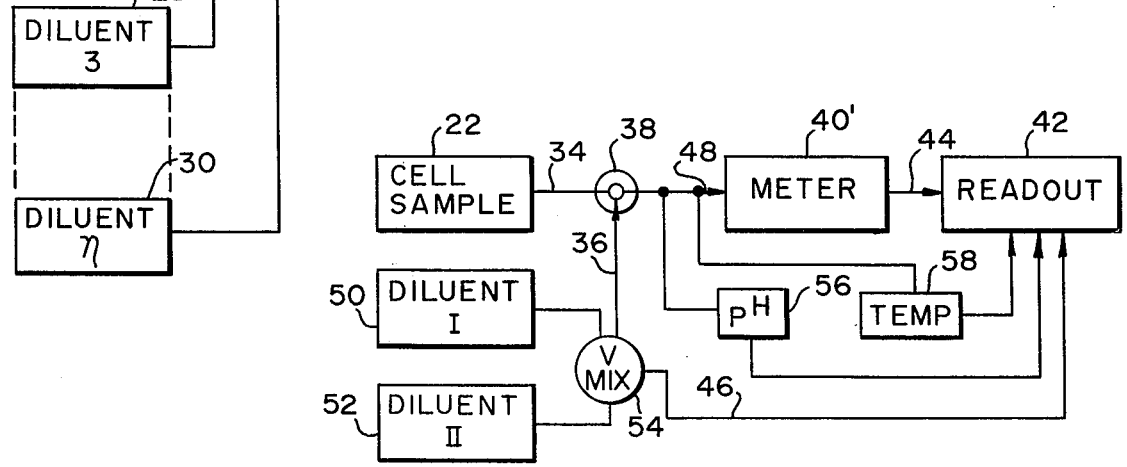
FIG. 3 is another embodiment of apparatus for generating the curves of FIG. 1.

FIG. 2 illustrates a semiautomatic apparatus for accomplishing my cell change test methodology. The test cells are red blood cells, only by way of example and are not to be considered a limitation to the scope of the invention. A blood sample, which can be in an isotonic solution, with anticoagulant if needed, is in a container 22. A plurality of different concentrations of a diluent, labeled as diluent 1, diluent 2, diluent 3, ... diluent n are in separate containers 24, 26, 28 and 30. The number of different diluent concentrations determines the number of data plotting points obtainable. Each diluent container feeds into a selecting valve 32, whereby any one diluent concentration can be selected at any one time. Means for advancing the diluent to the valve and for controlling valve selection position can be conventional and are not specifically illustrated. Output lines 34 and 36 from the blood sample container and selecting valve, respectively, feed into a mixing junction 38, at which location the hypotonic diluent and red blood cells mix and are advanced toward the measuring device, which in FIG. 2 is labeled resistance meter 40, but in FIG. 3 is labeled simply "meter" 40' to emphasize that it could be another form of cell parameter change detecting "meter," for example a cell volume measuring device. As previously mentioned, an MCV meter could be one of the several Coulter Counter ® particle analyzing instruments which measures MCV and also records the measured MCV for a batch or sample of blood cells. A readout device 42 could be such recording portion, or could be a curve plotter coupled to be controlled by the output data obtained from the resistance meter on a data line 44, in coordination with diluent selection information derived from the position of the selecting valve 32 and carried on an information line 46. Thus, the cell parameter change developed from each diluent will be obtained and recorded and can be plotted automatically. The position changing selection action of the valve 32 can be manual or automated, as by a motor drive within the skill of the art.

Because of the large number of red blood cells in even a small sample, a fraction, such as 0.02 microliter of blood, can be diluted by one ml of hypotonic diluent and be fed to the meter. The rate of feeding the diluted sample should be such that a determinably short time, for example approximately four seconds, elapses before the mixture reaches the meter 40, whereby the blood cells will have resided in the mixture long enough to have attained a certain parameter change, such as change in volume or resistance. The length of a conduit 48 coupling the mixing junction 38 to the input side of the meter can help determine the elapsed time and thus provide a repeatable time constant or delay, from sample to sample and batch to batch. Each separate sample batch can be processed and recorded in a very few seconds. Five to ten seconds of accumulative cell change data has proved sufficient.

Rather than pre-establish a complete set of diluents of known osmolality and/or concentration differences, as shown and described with reference to FIG. 2, the apparatus can be simplified and further automated by employing only two diluents, such as diluent I and diluent II, as shown in FIG. 3. One such diluent, such as diluent I, could be isotonic and be in a container 50. A container 52 would hold the diluent II, which could be distilled water. A proportional mixing arrangement, such as a mixing valve 54, which can be of conventional design, receives the two diluents and meters proportional amounts of same to form, one at a time, several possible concentrations. Such dilutions are carried discretely on the output line 36 to the mixing junction 38; then, the blood cells changed as batches having new parameter values are supplied to the meter 40 via the conduit 48. The operation of the meter 40', the readout device 42, and the data and information lines 44 and 46 can be the same as disclosed with reference to FIG. 2. The proportional mixing valve 54 can be controlled to develop many different concentrations over the full range of osmolalities, or a few within a narrow range, such as close to the peak 16 of the normal curve 10 in FIG. 1.

An alternative mode of operating the proportional mixing arrangement 54 would be to form a continuously changing concentration of the diluent. Thus, a continuously changing osmolality and resulting continuously changing cells would be achieved, and a continuous curve plotted as shown in FIG. 1, rather than a discrete plurality of cell parameter change values. If the change values were discrete, manual or automated curve point extrapolations would be needed to complete the curve segments. In FIG. 1, there are shown dots along the curves to indicate data points from which the curves could be developed from the discrete data values.

As earlier mentioned, a selected few concentrations or small range thereof could be informative as a screening tool. If the range of 120 to 175 mOsm is considered, for example, or even two or three points near 140 mOsm, the significant differences in both amplitude and relative direction of the curve segments therearound will be evident. In the manual practice of my cell parameter change test method, as well as the embodiments represented by FIGS. 2 and 3, small ranges of and/or selected osmolalities can be obtained and used for such screening purposes.

FIG. 3 also illustrates pH and temperature monitoring elements 56 and 58 coupled to be responsive to those respective aspects of the sample in the conduit 48 and, for example, controlling the readout device 42. Such elements also can be employed in the FIG. 2 embodiment. These monitors could sound an alarm, print an alarm condition, disable the readout, or even initiate a compensating procedure in the readout device 42, and/or the meter 40'.

From the foregoing, it now should be appreciated that my cell parameter change test method does not measure osmotic fragility or hemolysis, nor does it provide the same information as the prior art MCV measurement of red blood cells in only an isotonic solution. The test method and apparatus of my invention define and provide a new discriminator for cells in hematology, cytology, oncology, etc.

The hereinabove description, including the Figures, should enable those skilled in the art to understand and practice my invention and, to the extent which may be necessary under certain conditions, adapt same for optimal utilization, within the scope of the invention as defined by the appended claims.

What I claim and seek protection by U.S. Letters Patent is:

1. A method for testing cells comprising the steps of:
   a. forming a hypotonic mixture with at least one portion of a cell sample and a first solution having a specific osmolality, the cells of said sample each having an original parameter value state;
   b. causing the cells to reside in said mixture for at least a short known duration, during which the cells attain a change of at least one parameter value as compared to their original parameter value state, the amount of said change depending upon the osmolality of the mixture and the innate and acquired properties of each cell;
   c. measuring said attained cell parameter change; and
   d. employing said attained cell parameter change to define data which is capable of being compared with cell parameter change data representative of a known health or physiological condition.

2. The method according to claim 1 which includes: repeating the steps (a), (b) and (c) of claim 1 at least once, with a solution having an osmolality different than that of the first solution, each such repeating utilizing a solution of different osmolality; and employing the thus attained cell parameter change measurements to define a set of data which is capable of being compared with at least one set of cell parameter change data representative of at least one correspondingly known health or physiological condition.

3. The method according to claims 1 or 2 in which said step of measuring employs the principle of cell resistance measuring.

4. The method according to claims 1 or 2 in which said step of measuring obtains the volume change of the cells.

5. The method according to claims 1 or 2 in which said step of measuring obtains the apparent mean cell volume of the cells at each specific osmolality.

6. The method according to claims 1 or 2 in which said step of forming is with a solution having an osmolality such that the attained cell parameter change is proximate to that which is the maximum change achievable by the cell sample.

7. The method according to claims 1 or 2 in which said step of measuring includes correlating the maximum attained cell parameter change with the specific osmolality of the solution which provides that maximum cell change.

8. The method according to claims 1 or 2 in which said step of employing includes correlating the attained cell parameter change data with the original cell parameter value state so as to derive the percent of change relative to the original cell parameter value state.

9. The method according to claims 1 or 2 in which each said solution is of known pH.

10. The method according to claim 2 in which said step of employing includes forming a curve plotted from said defined set of data.

11. The method according to claim 2 in which each said hypotonic solution is formed from the combination of two diluents of different tonicity.

12. The method according to claim 11 in which at least one of said diluents is buffered sufficiently such that the pH of said solution remains substantially unchanged over a wide range of osmolalities.

13. The method according to claim 2 which includes the further step of: conducting the step a of claim 1 at least once with an essentially isotonic solution, for purposes of ascertaining said original parameter value state of the cell; and then conducting the steps b and c of claim 1 for obtaining the cell parameter change relative to the original cell parameter value state.

14. Apparatus for testing cells comprising: mixing means coupled to receive at least one portion of a cell sample and a first solution having a specific osmolality for forming therewith a hypotonic mixture, the cells of said sample each having an original parameter value state; timing means coupled to said mixing means for causing the cells of said sample to reside in said mixture for at least a short known duration, during which the cells attain a change of at least one parameter value as compared to their original parameter value state, the amount of said change depending upon the osmolality of the mixture and the innate and acquired properties of each cell; measuring means coupled to said mixing means for measuring the attained cell parameter change; and data defining means for employing said attained cell parameter change to define data which is capable of being compared with cell parameter change data representative of a known health or physiological condition.

15. Apparatus according to claim 14 which includes: control means coupled to solution supplying means for forming at least one other solution having an osmolality different than that of said first solution, whereby at least one other of said cell parameter value changes can be attained by the cells of said mixture and measured by said measuring means for defining a set of data which is capable of being compared with at least one set of cell parameter change data representative of at least one correspondingly known health or physiological condition.

16. Apparatus according to claims 14 or 15 in which said measuring means is constructed and arranged to employ the principle of cell resistance measuring.

17. Apparatus according to claims 14 or 15 in which said measuring means is constructed and arranged to obtain the volume change of the cells.

18. Apparatus according to claims 14 or 15 in which said measuring means is constructed and arranged to obtain the apparent mean cell volume of the cells at each specific osmolality.

19. Apparatus according to claims 14 or 15 in which said measuring means and said data defining means in combination are constructed and arranged for measuring and correlating the attained cell parameter change with the specific osmolality of the solution which provides that attained cell change.

20. Apparatus according to claims 14 or 15 which includes means for supplying an essentially isotonic diluent to said mixing means, whereby the original parameter value state of the cell sample can be ascertained by said apparatus.

21. Apparatus according to claim 15 in which said control means is constructed and arranged such that the mixture forming is with a solution having an osmolality such that the attained cell parameter change is proximate to that which is the maximum change achievable by the cell sample.

22. Apparatus according to claim 15 in which said control means and said data defining means are constructed and arranged for correlating the attained cell parameter change with the original cell parameter value state so as to derive the percent of change relative to the original cell parameter value state.

23. Apparatus according to claim 15 in which said control means is constructed and arranged such that each said hypotonic solution is formed from the combination of two diluents of different tonicity.

24. Apparatus according to claim 15 in which said control means is constructed and arranged such that each said hypotonic solution can be received from a discrete source thereof.

* * * * *